United States Patent [19]

Ilavazhagan et al.

[11] Patent Number: 6,083,506
[45] Date of Patent: Jul. 4, 2000

[54] PROCESS FOR THE PREPERATION OF SPERMICIDAL AGENTS AND OTHER BIOLOGICALLY ACTIVE MATERIALS

[75] Inventors: Govindaswamy Ilavazhagan; Chakra Devakumar, both of New Delhi, India

[73] Assignee: National Research Development Corporation, New Delhi, India

[21] Appl. No.: 09/014,703

[22] Filed: Jan. 28, 1998

[51] Int. Cl.[7] .......................... A61K 35/78; A01N 25/00
[52] U.S. Cl. .................. 424/195.1; 424/405; 514/841
[58] Field of Search ................................ 424/195.1, 405; 514/841

[56] References Cited

U.S. PATENT DOCUMENTS

| | | | |
|---|---|---|---|
| 4,515,785 | 5/1985 | Shimizu et al. | 424/195.1 |
| 5,196,197 | 3/1993 | Talwar et al. | 424/195.1 |
| 5,420,318 | 5/1995 | Lidert et al. | 554/193.1 |
| 5,501,855 | 3/1996 | Talwar et al. | 424/195.1 |
| 5,663,374 | 9/1997 | Nagasampagi et al. | 549/381 |

OTHER PUBLICATIONS

Biosis Abstract 1995:39264—Anti–implantation effect of neem oil, 1995.

*Primary Examiner*—Leon B. Lankford, Jr.
*Assistant Examiner*—Christopher R. Tate
*Attorney, Agent, or Firm*—Venable; George H. Spencer; Charles C. Rories

[57] ABSTRACT

A process for the preparation of spermicidal agents and other biologically active materials from neem oil or extractives by subjecting a neem feed obtained from neem oil to the step of enrichment. Such a step of enrichment is carried out in a chromatographic column containing a sorbant, and the feed is eluted with a non polar followed by a polar solvent or mixtures thereof. In accordance with one embodiment, the feed is formed by subjecting neem oil to the step of solvent partition, the precipitate being removed therefrom and the filterate forming the feed. In accordance with another embodiment, the feed is formed by adding a polar solvent to the filterate of the first embodiment, the lower layer formed therefrom being subjected to the step of distillation for removal of the solvent to obtain a feed.

9 Claims, No Drawings

6,083,506

PROCESS FOR THE PREPERATION OF SPERMICIDAL AGENTS AND OTHER BIOLOGICALLY ACTIVE MATERIALS

FIELD OF INVENTION

This invention relates to a process for the preparation of a spermicidal agent and other biologically active materials such as odour and pesticide free neem oil, neem pesticides and antifertility agents from neem oil or extractives.

PRIOR ART

In modern times several biological activities and utilities such as spermicidal action, pesticidal activity, utility as urea fertilizer additive, neem oil in soap and cosmetics have been enumerated. Each and every commercial application employs mostly total neem oil or neem seed extractives with little or no modification. A method for the preparation of spermicidal agent from neem oil involves steam distillation which is time consuming and at the same time renders the whole of the valuable product present in the neem material a waste. Similarly the method of the preparation of neem pesticides does not give consideration to the utility of contraceptive agents present in them.

OBJECTS OF THE INVENTION

An object of this invention is to propose a process for the preparation of a spermicidal agent, antiferitlity agents, pesticides and odour- and pesticide-free neem oil from neem oil which obviates the disadvantages associated with those of the prior art.

Yet another object of this invention is to propose a process for the preparation of a spermicidal agent, antifertility agents, pesticides and odour/pesticide free neem oil from neem oil and extractives which has the required level of activity.

DESCRIPTION OF INVENTION

According to this invention there is provided a process for the preparation of spermicidal agent and other biologically active neem materials from neem feed obtained from neem oil, subjecting said feed to the step of enrichment by introduction into a chromatographic column containing a known sorbant such as herein described eluting with a non polar solvent followed by a polar solvent or mixtures thereof with or without non polar solvents to obtain the spermicidal agent and the antiferitility agents, neem pesticides and neem oil free from odour.

Reference to neem oil is intended to imply neem oil and/or extractives.

The process of the present invention broadly consists of forming a neem feed by the step of solvent partition, which is then subjected to the step of enrichment by solution in chromatographic column.

In accordance with a first embodiment of this invention the feed is formed by the step of solvent partition by mixing neem oil with a solvent having a boiling point of up to 120° C. Preferably, the solvent comprises an aliphatic hydrocarbon such as n-hexane or other known hydrocarbons. The ratio of neem oil to solvent is 0.5:1 to 1:5. The solvent added to neem oil can be of light, middle or heavy fractions. Though all three fractions may be employed in the process of the present invention, it is preferred that the middle fraction may be employed as the loss is less and the solvent can be recycled. If the light fraction is used the boiling point is less than 60° C. and consequently, the loss is more in comparison to that of middle fraction. The heavy fraction has a boiling point of 110 to 120° C. and hence, greater energy is required for recovery of the solvent.

The step of solvent partition is carried out at room temperature. However, lower temperatures are preferred as this enhances the number of bitter constituents that are biologically valuable that precipitate from the solution. The precipitate constitutes the enriched biodegradable herbal pesticides. Thus if the step of partition is effected at 10° C., it is estimated that in as such as 50% of the bitter constituents are removed by precipitation. Preferably, the step of solvent partition is carried out at a temperature of 0 to 15° C. The step of solvent partition is carried out for a period of 15 to 60 minutes and preferably from 15 to 30 minutes. The step of solvent partition results in a precipitate, which is removed, and the filtrate forms the first feed of the first embodiment.

In the second embodiment for preparation of the feed, a polar solvent such as ethanol or methanol present in 0 to 10% of water is added to the filtrate of the first embodiment.

Such a polar solvent is added to the filtrate in the ratio of 1:1 to 1:5 and preferably 1:3. Such a step is carried out at a temperature of 10 to 40° C. and, for example, in a separating vessel. Two layers are produced in the separating vessel. The upper layer is the hydrocarbon layer and containing most of the glycerides which are not required in the spermicidal agent of the present invention. The lower layer is an alcohol layer containing the odiferous constituents and the remaining bitter constituents. The lower layer is removed and additional polar solvent is added to the upper layer, and which step may be further repeated several times. Such a step of adding a polar solvent to the upper layer is repeated as a certain amount of odoriferous components are still retained in the upper layer. Alternatively, and in the instance where such a step is carried out in a counter flow column, the polar solvent layer is recycled several times.

The lower layer obtained from the aforesaid step is then subjected to the step of distillation for removal of solvent under atmospheric pressure or moderate vaccum to obtain a concentrated extract. The concentrated extract constitutes the feed of the second embodiment.

The feed of the first or second embodiment is subjected to the step of enrichment by introduction into a column packed with a sorbant such as silica gel, fluorisil, alumina and/or flurodin earth and having a mesh size of preferably 60–400 and eluted with a solvent mixture having an increasing polarity. Thus, initially the solvent comprises a non polar solvent such as hexane, benzene, toluene or ligroin. Finally, the solvent comprises a polar solvent and/or a binary mixture of the non polar and polar solvent. By way of example, the polar solvent is selected from acetone, ethyl acetate, chloroform methanol or methylene chloride.

Different fractions are collected from the column and the solvents are then removed by distillation. Odour and pesticide free neem oil is obtained from fractions eluted with solvent mixture containing in the ratio of hydrocarbon to, the other solvent (100% to 80% hydrocarbon).

Spermicidal agent is eluted with a binary mixture consisting of non polar and polar solvent in the ratio of 4:1 to 1:1. Anti-fertility agents are eluted with a binary mixture containing 20–50% by v/v of non polar solvent, the remainder being the polar solvent.

Neem pesticides are eluted with a polar solvent mixture containing 0–20% of another polar solvent.

Further objects and advantages of this invention will be more apparent from the ensuing example, which is however is not to be construed in a restrictive manner.

EXAMPLE 1

To 50 g of neem seed extractive in a 500 ml conical flask 50 ml of chilled n-hexane was added, the contents were shaken as vigorously as possible for a few minutes and left aside for 15 min. The supernatant hexane solution constitutes the feed of the first embodiment was loaded on to a chromatographic column containing 1,500 g of silica gel G (60–120 mesh) and eluted with 5 litres of each hexane, hexane-ethyl acetate (9:1), hexane-ethyl actate (4:1), hexane-ethyl acetate (3:1), hexane-ethyl acetate (1:1), ethyl acetate, ethyl acetate-methanol (4:1), ethyl acetate-methanol (1:1) and methanol in that order. 500 ml fractions were collected and distilled under 50 C. in rotary vacuum evaporator. Almost colourless to tan yellow, odour and pesiticide-free neem oil (15–40 g) was obtained from fractions eluted with hexane containing 0–10% methanol. The spermicidal agent was obtained as odourifercous golden yellow light oil (2–5 g) from fractions eluted with hexane-ethyl acetate (4:1). The antifertility agents (2–5 g) were obtained during elution withethyl acetate containing 30–50% hexane. The precipitate obtained in the first step of the process constitutes an additional source of neem pesticide.

EXAMPLE 2

To 1074 gms of neem extractive, 5 litres of n-hexane were added and stirred to get granular light brown precipitate. The mixture was filtered to separate precipitate (156 gms). This precipitate was found useful as a herbal pesticide. The filtrate was concentrated to obtain residues (918 gms). The residues were dissolved in 1 litre of n-hexane and the hexane solution was thrice extracted each time with 2 litres of aqueous ethanol containing 10% water.

The extracts were pooled and concentrated in vacuo to obtain dark brown syrup (170 gms) and the hexane solution on distillation of solvent left behind provided neem lepid (745 gms).

The syrupy residue (170 gms) obtained above consititutes as a feed for column chromatography. A 50 gram portion of this feed was subject to chromophotography the procedure enumerated under example 1 to obtain various active fractions.

In-vitro Spermicidal Activity of the Agent

The results of the studies on the in vitro spermicidal activity of various doses of the spermicidal agent of the present invention is given in the Table 1. The minimum effective concentration (MEC) in case of rat spermatozoa was found to be 0.5mg/ml. In case of monkey and human serum 25mg/ml was able to kill all the sperms within 20 seconds of mixing. The spermatozoa in all the above tests were immobilised and did not regain their motality when incubated with saline buffered with glucose. This shows that the agent is spermicidal and not spermiostatic. The susceptibility of rat spermatozoa are different from that of monnkey and human semen, the former being more susceptible because very low concentration (0.5 mg/ml) is enough to kill the spermatozoa within 20 sec. This may be due to the species difference.

TABLE 1

In vitro spermicidal activity of spermicidal agent of the present invention

| Conc. | Human semen | Monkey semen | rat spermatozoa |
|---|---|---|---|
| 25.00 mg/ml | – | – | – |
| 20.00 mg/ml | ++ | ++ | – |
| 15.00 mg/ml | +++ | ++ | – |
| 10.00 mg/ml | ++++ | +++ | – |
| 5.00 mg/ml | ++++ | ++++ | – |
| 2.50 mg/ml | ++++ | ++++ | – |
| 1.25 mg/ml | ++++ | ++++ | + |
| 1.00 mg/ml | ++++ | ++++ | +++ |
| 0.50 mg/ml | ++++ | ++++ | ++++ |

– No motility
+ 25% motile
++ 25 to 50% motile
+++ 50 to 80% motile
++++ 80% motile Antifertility Effect of Bitter
Preparation of the Antifertility Aqent The required amount of the bitter was dissolved in about 0.5ml of ethanol and diluted with 0.5ml of distilled water. The mixture was shaken well before feeding. The studies were done on the rats.

Adult female rats on the day of proestrous, were caged with proven fertile males in the ratio of 3:1 and their vaginal smear was examined the following morning. The presence of the sperm in the smear was considered as proof of mating and it was designated as day 1 of the pregnancy, these mated female rats were used in the following studies.

Antifertility Activity

The two fractions were studied for their antifertility activity when administered orally in experimental animals. Various doses were tried by calculating the dose according to the output from the fraction and the best dose was selected and administered orally. The dose was given on day 1–7 (prior to implantation) and from day 5–11 (post implantation).

Antifertility Effect

The antifertility activity of a first fractions was found to have maximum activity (preimplantation) when administered orally at a dose of 12 mg/ml per day to rats on Day 1–7 and of a second fraction was found to have post implantation activity at a dose of 7 mg/ml/day on Day 5–11. (Table 1). Thus, the first fraction has antiimplantaticin effect and the second fraction has abortifacient effect.

TABLE 1

Effect of Antifertility agents

| AGENT NO. | Dose (mg/ml/day) | Pre-implantation D1–D7 (%) | Post-implantation (D5–D11) (%) |
|---|---|---|---|
| First agent | 12.0 | 100 | 40 |
| Second agent | 7.0 | 25 | 100 |

Doses of various fractions calculated according to the output from the total bitter.

We claim:

1. A process for fractionating a feed solution derived from neem oil comprising:
    a) obtaining said feed solution by a solvent partition process comprising mixing neem oil with a neem oil-miscible solvent so that a precipitate forms, and filtering the mixture to separate the precipitate from the liquid filtrate, in which the liquid filtrate is said feed solution;

b) contacting said feed solution with an adsorbent chromatographic sorbant;

c) eluting with a non-polar solvent; and d) further eluting said chromatographic sorbant and collecting separate fractions comprising (1) odor-free, pesticide-free neem oil, (2) a spermicidal agent, (3) an antifertility agent, and (4) a pesticide, wherein said odor-free, pesticide-free neem oil is obtained by eluting with a binary mixture comprising 80% to 100% non-polar solvent and 0% to 20% non-polar solvent;

wherein said spermicidal agent is obtained by eluting with a binary mixture comprising a non-polar solvent and a polar solvent present in a volume/volume ratio of 4:1 to 1:1;

wherein said antifertility agent is obtained by eluting with a binary mixture containing a non-polar solvent and a polar solvent present in a volume/volume ratio of 1:4 to 1:1; and wherein said pesticide is obtained by eluting with a polar solvent or with a binary mixture comprising a polar solvent and up to 20% (volume/volume) of another polar solvent.

2. The process of claim 1 wherein said neem oil-miscible solvent consists of aliphatic hydrocarbons;

and wherein the volume/volume ratio of said solvent to neem oil is 1:2 to 1:5.

3. The process of claim 1 wherein said solvent partition process is carried out at 0° C. to 15° C. for a time period of 15 to 60 minutes.

4. The process of claim 1 wherein said sorbant has a mesh size ranging from 60 to 400.

5. The process of claim 1 wherein said non-polar solvent is selected from the group consisting of hexane, ligroin, toluene, benzene, and a mixture of toluene and benzene;

and wherein said polar solvent is selected from the group consisting of ethyl acetate, chloroform, methanol, methylene chloride, and methanol.

6. A process for fractionating a feed solution derived from neem oil comprising:

a) obtaining said feed solution by an extraction process comprising:

(i) mixing neem oil with an oil-miscible solvent so that a precipitate forms, and filtering the mixture to separate the precipitate from the liquid filtrate;

(ii) mixing said liquid filtrate with a polar solvent which is immiscible with said liquid filtrate, allowing the liquids to separate into two layers, and removing the polar solvent layer;

(iii) repeating step (ii) one or more times by mixing the filtrate layer with more of said polar solvent, allowing the liquids to separate into two layers, and again removing the polar solvent layer; and pooling said polar solvent layers;

(iv) removing solvent from said pooled polar solvent layers to produce a concentrated solution, in which the concentrated solution is said feed solution;

b) contacting said feed solution with an adsorbent chromatographic sorbant;

c) eluting with a non-polar solvent; and d) further eluting said chromatographic sorbant and collecting separate fractions comprising (1) odor-free, pesticide-free neem oil, (2) a spermicidal agent, (3) an antifertility agent, and (4) a pesticide, wherein said odor-free, pesticide-free neem oil is obtained by eluting with a binary mixture comprising 80% to 100% non-polar solvent and 0% to 20% non-polar solvent;

wherein said spermicidal agent is obtained by eluting with a binary mixture comprising a non-polar solvent and a polar solvent present in a volume/volume ratio of 4:1 to 1:1;

wherein said antifertility agent is obtained by eluting with a binary mixture containing a non-polar solvent and a polar solvent present in a volume/volume ratio of 1:4 to 1:1; and wherein said pesticide is obtained by eluting with a polar solvent or with a binary mixture comprising a polar solvent and up to 20% (volume/volume) of another polar solvent.

7. The process of claim 6 wherein the polar solvent of step (ii) is an alcohol/water mixture for which the ratio of alcohol to water is 1:1 to 95:5, and wherein the alcohol is selected from the group consisting of ethanol and methanol;

wherein the volume/volume ratio of said solvent to filtrate is 1:1 to 1:5;

and wherein steps (i)–(iii) of claim 6 are carried out at a temperature of 10° C. to 40° C.

8. The process of claim 6 wherein said sorbant has a mesh size ranging from 60 to 400.

9. The process of claim 6 wherein said non-polar solvent is selected from the group consisting of hexane, ligroin, toluene, benzene, and a mixture of toluene and benzene;

and wherein said polar solvent is selected from the group consisting of ethyl acetate, chloroform, methanol, methylene chloride, and methanol.

* * * * *